(12) United States Patent
Morgan

(10) Patent No.: US 8,631,807 B2
(45) Date of Patent: Jan. 21, 2014

(54) METHOD AND APPARATUS FOR ORTHODONTIC FLOSS AID

(75) Inventor: Laura J. Morgan, Round Rock, TX (US)

(73) Assignee: A Better Way of Life, Inc., Missoula, MT (US)

( * ) Notice: Subject to any disclaimer, the term of this patent is extended or adjusted under 35 U.S.C. 154(b) by 348 days.

(21) Appl. No.: 12/049,195

(22) Filed: Mar. 14, 2008

(65) Prior Publication Data

US 2008/0223398 A1  Sep. 18, 2008

Related U.S. Application Data

(60) Provisional application No. 60/906,779, filed on Mar. 14, 2007.

(51) Int. Cl.
*A61C 15/00* (2006.01)

(52) U.S. Cl.
USPC ............................ 132/323; 132/324; 132/329

(58) Field of Classification Search
USPC ......... 132/321, 323, 324, 325, 328, 329, 309, 132/326, 327, 322; 433/143; D28/65–68
See application file for complete search history.

(56) References Cited

U.S. PATENT DOCUMENTS

| | | | | | |
|---|---|---|---|---|---|
| 1,332,170 | A | * | 2/1920 | Elzinga | 132/324 |
| 1,607,061 | A | * | 11/1926 | Deming | 132/325 |
| 1,733,631 | A | * | 10/1929 | Spiegel et al. | 132/324 |
| 2,517,806 | A | * | 8/1950 | Streiler | 132/309 |
| 3,309,773 | A | * | 3/1967 | Weller | 433/3 |
| 3,376,876 | A | * | 4/1968 | Wicklund | 132/324 |
| 3,939,853 | A | * | 2/1976 | Spanondis | 132/323 |
| 4,005,722 | A | * | 2/1977 | Bragg | 132/324 |
| D251,075 | S | * | 2/1979 | Schiff | D28/68 |
| 4,167,063 | A | * | 9/1979 | Sosnay | 433/3 |
| 4,304,246 | A | * | 12/1981 | Yafai | 132/323 |
| 4,597,398 | A | * | 7/1986 | Chu | 132/324 |
| 4,706,694 | A | * | 11/1987 | Lambert | 132/323 |
| 5,125,424 | A | * | 6/1992 | Eisen | 132/323 |
| 5,183,064 | A | | 2/1993 | Barth | |
| 5,184,631 | A | * | 2/1993 | Ikeda | 132/323 |
| 5,327,977 | A | * | 7/1994 | Lukashuk | 172/376 |
| 5,375,615 | A | * | 12/1994 | Wahlstrom | 132/325 |
| 5,482,466 | A | * | 1/1996 | Haynes | 132/323 |
| 5,573,021 | A | * | 11/1996 | Grofcisk et al. | 132/324 |
| 5,738,125 | A | * | 4/1998 | Lin | 132/323 |
| 5,860,434 | A | * | 1/1999 | Sines et al. | 132/323 |

(Continued)

FOREIGN PATENT DOCUMENTS

GB 2183485 A * 6/1987
WO WO0158380 8/2001

*Primary Examiner* — Vanitha Elgart
(74) *Attorney, Agent, or Firm* — David Johnson

(57) ABSTRACT

A flossing tool for persons wearing braces. A floss support head is attached at an acute angle with respect to a handle. The head includes two spaced-apart support elements where the first support element closest to the handle is thinner than the distance between the teeth and the arch-wire. A disposable plastic embodiment includes a floss strand affixed in an injection molding process to ends of the support elements; a tapered portion of the first support element which allows the device to pivot without interference from the arch-wire; and a broadened spatula tip for securing an end of the floss strand. The end of the first support element may be curved outwardly. Another embodiment includes a wire head with floss support loops.

4 Claims, 8 Drawing Sheets

(56) References Cited

U.S. PATENT DOCUMENTS

| | | | |
|---|---|---|---|
| 6,006,762 A * | 12/1999 | Hsia | 132/327 |
| 6,065,479 A * | 5/2000 | Chodorow | 132/323 |
| 6,076,535 A * | 6/2000 | Yipp | 132/324 |
| 6,209,550 B1 * | 4/2001 | Powell, Jr. | 132/323 |
| 7,077,653 B2 * | 7/2006 | Haab | 433/143 |
| 7,328,711 B2 * | 2/2008 | Hill | 132/323 |
| 7,997,287 B2 * | 8/2011 | Jansheski et al. | 132/323 |
| 2004/0354400 | 2/2004 | Cheng | |
| 2007/0017546 A1 * | 1/2007 | Brown | 132/323 |
| 2007/0246061 A1 * | 10/2007 | Hirai | 132/328 |
| 2008/0149134 A1 * | 6/2008 | Crossman | 132/324 |
| 2008/0185016 A1 * | 8/2008 | Jansheski et al. | 132/324 |
| 2009/0188519 A1 * | 7/2009 | Vanbuskirk et al. | 132/309 |
| 2010/0163072 A1 * | 7/2010 | Shinzato | 132/324 |
| 2012/0167913 A1 * | 7/2012 | Caldwell | 132/323 |

* cited by examiner

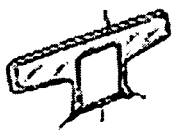
FIG. 1 – PRIOR ART
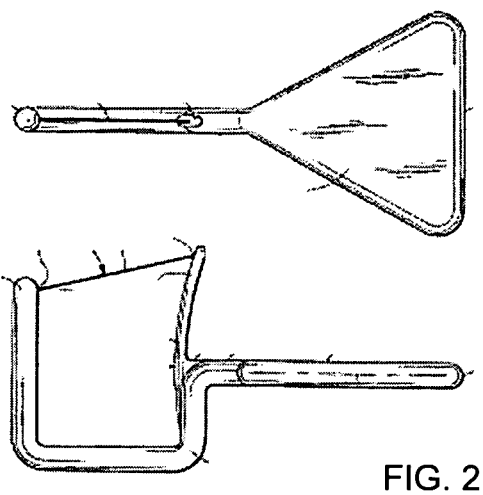
FIG. 2A – PRIOR ART
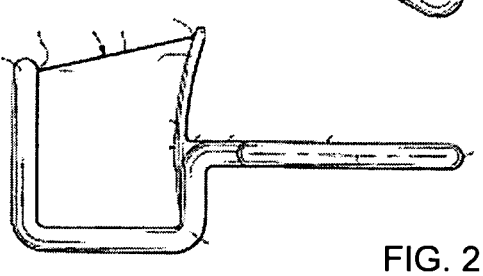
FIG. 2B – PRIOR ART
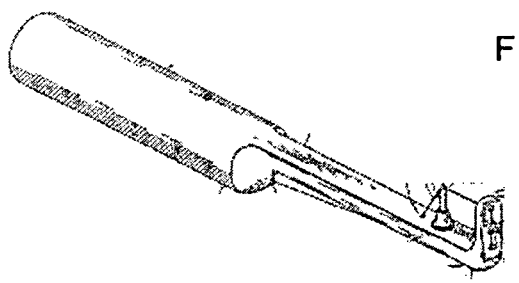
FIG. 3 – PRIOR ART

METHOD AND APPARATUS FOR ORTHODONTIC FLOSS AID

This Non-Provisional patent application is related to U.S. Provisional Application No. 60/906,779 filed Mar. 14, 2007 by applicant Laura Morgan, and claims the benefit of that filing date.

BACKGROUND

1. Field of Invention

The current invention relates to a device and method for flossing between the teeth of a person. More particularly, the current invention relates to a floss device which can direct floss between teeth behind the arch-wire of a person who wears orthodontic braces.

2. Prior Art

Regular flossing is recognized as being very important to oral hygiene and health.

One method of flossing is to wind floss around fingers and to guide the floss between the teeth. This method does not work well for persons who wear braces, because it is difficult to direct floss behind the arch-wire of the braces. One method of flossing with braces requires the threading of the floss behind the arch-wire. This process is time consuming because it must be repeated for each gap between adjacent teeth.

Prior Art Floss Picks

Another method of flossing is to provide disposable floss devices such as DenTek™ floss picks which support a strand of floss between a pair of posts or arms. Many of these prior art devices have posts or arms which are too thick to be directed between the arch-wire and the teeth, so those devices may not be used by persons who wear braces.

Single Floss Support Devices

U.S. Pat. No. 4,597,398, to Chu describes a tool with a floss support post that may be inserted behind the arch-wire. The user grasps another portion of the floss.

U.S. Pat. No. 7,328,711 to Hill describes an orthodontic flossing implement with an arm which has a floss support portion insertable underneath the arch of a brace wire.

Dual Floss Support Devices

U.S. Pat. No. 5,101,843 to Peng describes a disposable flosser with two curved floss arm supports as shown in FIG. 1.

U.S. Pat. No. 5,860,434 to Sines et al. describes several embodiments of flossing devices including one which has an arm with a straight support and a curved support, and a grip which is orthogonal to the supports. FIGS. 2A and 2B show this device.

U.S. Pat. No. 5,482,466 to Haynes describes a flossing instrument which includes a combination floss spool cavity and handle to which is connected an arm with two floss supports, traversely mounted at a distal end of the arm remote from the handle. One support forms a tower which fits behind the arch-wire. FIG. 3 shows this device. There is a need for a floss device which permits better floss access for persons who wear braces. There is a need for a floss device which has a deep head oriented at an angle with respect to the device handle in order to permit floss to be delivered to deep pockets.

There is a need for a floss device which permits improved access to rear teeth. One aspect of the current invention is that a floss support head is provided at an acute angle with respect to the handle as opposed to prior art devices which typically provide floss support heads that are orthogonal to the device handles. In the current invention, the orientation of the head provides improved access to the rear teeth, and it is particularly easy for children to use in order to floss effectively.

SUMMARY OF INVENTION

The current invention provides a floss support head which is attached at an acute angle with respect to a handle. This orientation of the head with respect to the handle permits easier access to interproximal spaces in both the front and the rear of the mouth. A combination of a deep U-shaped floss support head and the angled head permits effective flossing of deep pockets in all areas of the mouth.

In one embodiment, the floss support head is constructed of bent wire, such as a 0.035" (0.9 mm) diameter orthodontic wire. Loops are formed in the end of the wire to support a floss strand.

In another embodiment, the floss support had and a handle are injection molded as a disposable single part, and a floss strand is molded between two floss support elements of the floss support head. In one example, one of the floss support elements is provided as a thin plastic portion having a thickness of less than about 0.04 inches (1 mm). A tapered portion of the first support element allows the device to pivot between the arch-wire and the teeth without interference from the arch-wire. A broadened spatula tip is provided for securing an end of the floss strand. The end of the first support element may be curved outwardly.

The floss devices are used by inserting the upper portion of the first floss support element behind the arch-wire, directing the tip of the first floss support element along a tooth toward the gum line, and then moving the handle up and down to create a flossing action.

BRIEF DESCRIPTION OF THE DRAWINGS

FIG. 1 is a perspective view of a prior art floss device described in U.S. Pat. No. 5,101,843 to Peng.

FIG. 2A is a top view of a prior art floss device as described in U.S. Pat. No. 5,860,434 to Sines et al.

FIG. 2B is a side view of the prior art floss device of FIG. 2A.

FIG. 3 is a perspective view of a prior art floss device described in U.S. Pat. No. 5,482,466 to Haynes

DETAILED DESCRIPTION OF INVENTION

Element List

Figure 4A:
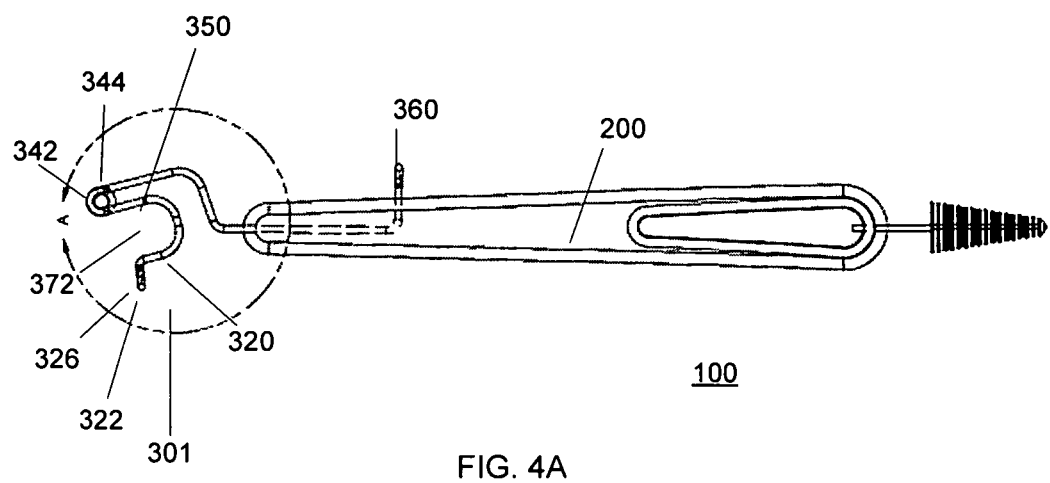
FIG. 4A is a side view of a first embodiment of the current invention.

The following element list refers to all element numbers in the figures and in the description for all embodiments.

teeth 40, 41
interproximal space 50
arch-wire 60
dental flossing device 100, 101
handle 200, 201
handle axis of alignment 220, 221
handle flat grip portion 222
handle grip plane 224
brush 230
pick brush 231
floss support head 301, 302
bent wire floss support head 301
plastic floss support head 302
plane of the head 306
floss support head axis of alignment 310
acute angle A 311, 312 of floss support head
first floss support element 320, 321
first floss retention distal end 322, 323
first floss retention distal end thickness 324
maximum width 325 of the first floss retention distal end
first floss retention distal end loop 326
first support axis of alignment 328
second support axis of alignment 329
first floss retention end loop angle 327
first support section 330, 331
first support section thickness 332
first support section tapered portion 334
second support section 340
second floss retention distal end 342, 343
second floss retention distal end loop 344
second support element 350, 351
floss guide 360
floss head U-shape 372, 373
floss strand 400, 401
floss strand first end 410
floss strand second end 420

DETAILED DESCRIPTION OF EMBODIMENT

Floss Device with Wire Frame Head

Figure 4B:
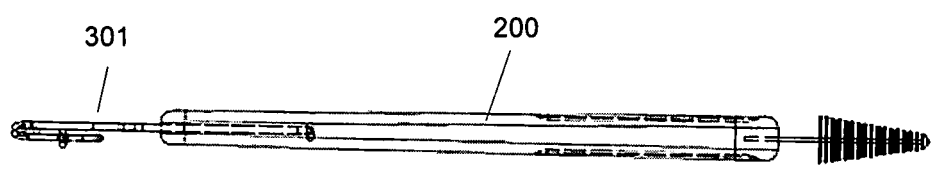
FIG. 4B is a top view of the embodiment of FIG. 4A.

FIGS. 4A and 4B are a side view and top view of a first embodiment of a dental flossing device 100 of the current invention with a handle 200 and a bent wire floss support head 301. In this embodiment, the floss support had has a U-shape 372 with a first floss support element 320 supporting a first floss retention distal end loop 326 at the first floss retention distal end 322, and a second support element 350 supporting a second floss retention distal end loop 344 at the second floss retention distal end 342.

Figure 4C:
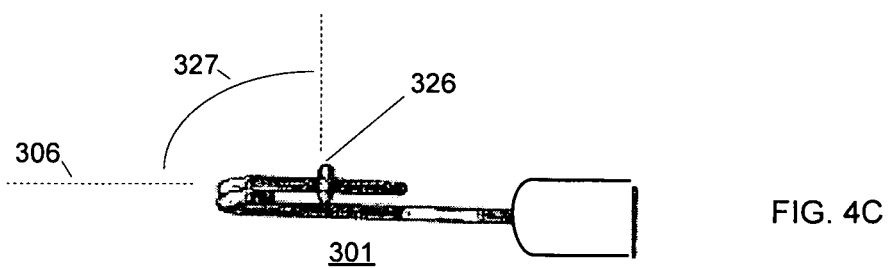
FIG. 4C is a detailed view of the floss support head of the embodiment of FIG. 4A.
Figure 4D:
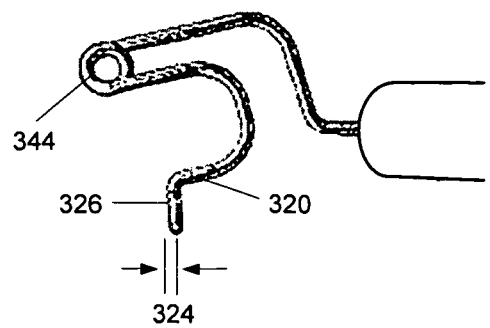
FIG. 4D is a detailed view of the floss support head of the embodiment of FIG. 4A.

FIGS. 4C and 4D are detailed views of the floss support head of the dental flossing device 100. In this embodiment, the first floss retention distal end loop 326 forms a first floss retention end loop angle 327 with respect to the head plane 306. In this example, the first floss retention distal end loop 326 is orthogonal to the plane of the head 306. FIG. 4D illustrates the thickness 324 of the floss retention distal end loop 326 and the first floss support element 320. The floss support head may be constructed of bent wire, such as a 0.035" (0.9 mm) diameter orthodontic wire.

Figure 5A:
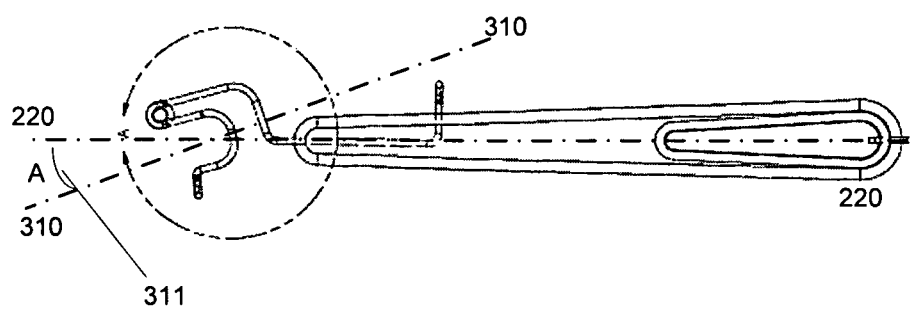
FIG. 5A is a side view of the embodiment of FIG. 4A showing an acute angle A between axes of alignment for the handle and the floss support head.

FIG. 5A is a side view of the embodiment of the dental flossing device 100 showing an acute angle A (311) between the floss support head axis of alignment 310 and the handle axis of alignment 220. In this example, the angle A is approximately 20 degrees. In other examples, an angle in the range of 10 to 80 degrees may be employed.

Figure 5B:
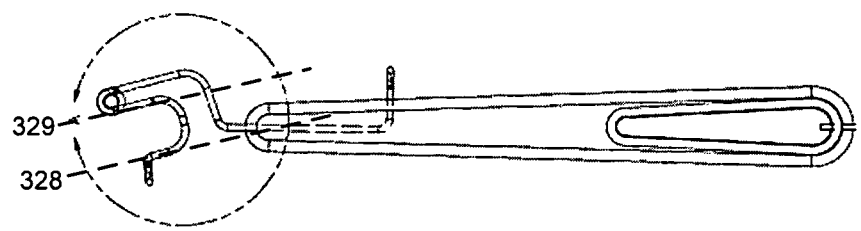
FIG. 5B is a side view of the embodiment of FIG. 4A showing a first support axis of alignment and a second support axis of alignment.

FIG. 5B is a side view of the embodiment of the dental flossing device 100 showing a first support axis of alignment 328 and a second support axis of alignment 329.

Figure 6:
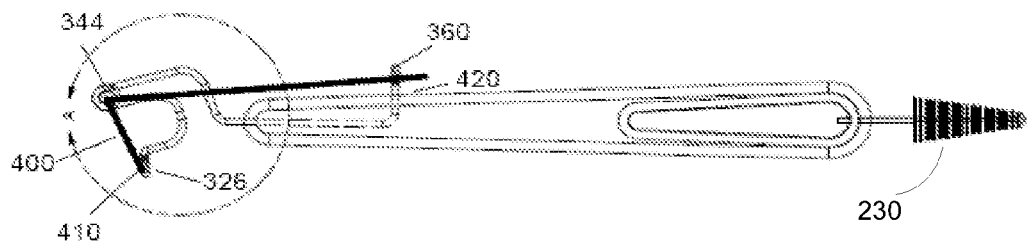
FIG. 6 is a side view of the embodiment of FIG. 4A showing a strand of floss affixed to the device.

FIG. 6 is a side view of the embodiment of the dental flossing device 100 showing a strand of floss 400 affixed to the device. In this example, a floss strand first end 410 is threaded through the second floss retention distal end loop 344 and tied to the first floss retention distal end loop 326. The floss strand second end 420 is wrapped around the floss guide 360.

Method of Use—Bottom Teeth

In this embodiment, a floss strand 400 of a few inches of floss is removed from a roll of floss. A first end 410 of the floss strand is threaded through the second floss retention distal end loop 344 and tied to the first floss retention distal end loop 326. The floss is then either pulled tight and held against the handle by the user, or wrapped around the floss guide 360 knob on the handle.

The following steps are repeated for each interproximal area:

To insert the first floss support element 320 behind the arch-wire, the handle 200 is held in a horizontal plane slightly above the lower teeth. The first floss retention distal end loop 326 is positioned interproximally and slid toward the gum-line. If the user is flossing the tooth on the user's right of the interproximal area, then the handle is moved to the user's right. If the user is flossing the tooth on the user's left of the interproximal area, then the handle is moved to the user's left.

Assuming that the user starts with the tooth on the user's right of the interproximal area, the handle is rotated to the right. To begin the flossing operation, the handle is tilted upward approximately 45 degrees, and the handle is moved down to slide the floss down into the gum sulcus or pocket. The deep U-shape of this embodiment, and the orientation of the head with respect to the handle permit access to the full depth of the pockets. The handle is then moved up and down 2 or three times to slide the floss up and down in the gum sulcus or pocket.

To floss, the tooth on the user's left, the handle is rotated to the left. To begin the flossing operation, the handle is tilted upward approximately 45 degrees, and the handle is moved down to slide the floss down into the gum sulcus or pocket. The handle is then moved up and down 2 or three times to slide the floss up and down in the gum sulcus or pocket.

To remove the device, the handle is lowered to a horizontal plane and then lifted to lift the first floss retention distal end loop 326 above the arch-wire and teeth.

An interdental brush 230 may be attached to the opposite end of the handle and may be used to clean around orthodontic brackets and open spaces.

Method of Use—Top Teeth

Each interproximal area is flossed in a manner similar to the bottom teeth, except that to insert the first support behind the arch-wire, the handle is held in a horizontal plane slightly below the upper teeth. The first floss retention distal end loop 326 is positioned interproximally and slid toward the gumline. The handle is rotated to the right or left as described above. To begin the flossing operation, the handle is tilted downward approximately 45 degrees, and the handle is moved up to slide the floss up into the gum sulcus or pocket. The handle is then moved up and down 2 or three times to slide the floss up and down in the gum sulcus or pocket. To remove the device, the handle is raised to a horizontal plane and then lowered to lower the first end loop below the arch-wire and teeth.

DETAILED DESCRIPTION OF EMBODIMENT

Floss Device with Plastic Head

Figure 7:
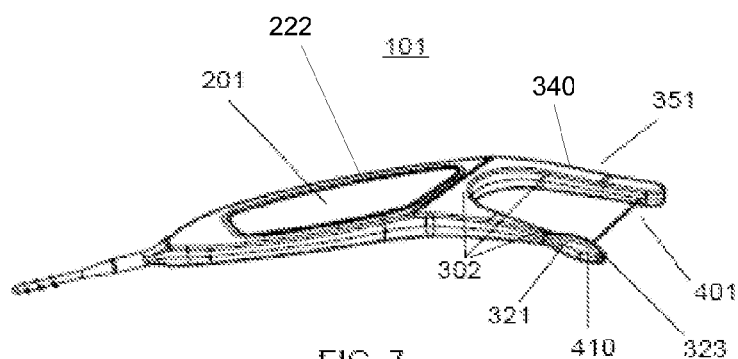
FIG. 7 is a perspective view of another embodiment of the current invention.
Figure 8:
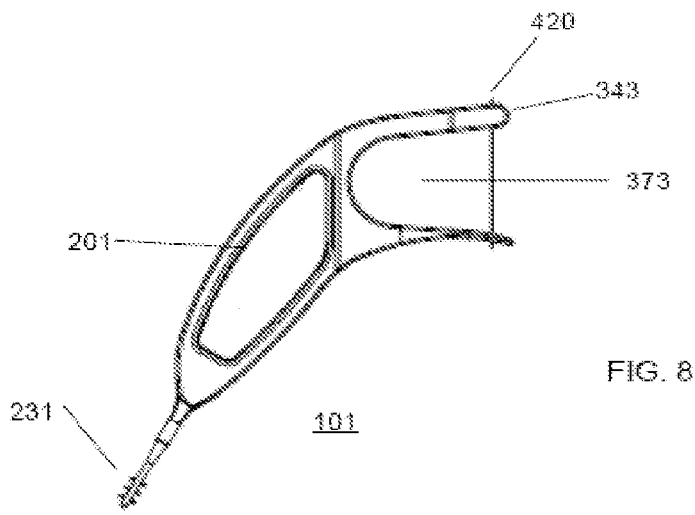
FIG. 8 is a front view of the embodiment of FIG. 7.

FIGS. 7 and 8 are a perspective and a front view of another embodiment of the current invention.

In this embodiment, the dental flossing device 101 comprises a plastic floss support head 302 integral to a handle 201, which permits the device to be injection molded as a single part. In this embodiment, the floss support head 302 has a U-shape 373.

The floss support head includes a second support element 351 and a first floss support element 321. A floss strand 401 is affixed to the device so that the floss strand first end 410 is attached at the first floss retention distal end 323, and the floss strand second end is attached at the second floss retention distal end 343.

In this example, a pick brush 231 attached to the handle. The pick brush has a few short bristles so that it can serve as either a brush or a pick in order to clean around the sides of the braces and brace brackets. In this example, the pick brush has a diameter of about 0.03 inches (0.8 mm) so that it can clean debris from between the teeth or in the brace area. The smaller bristles require less cleaning of debris than a brush with longer bristles.

Figure 9:
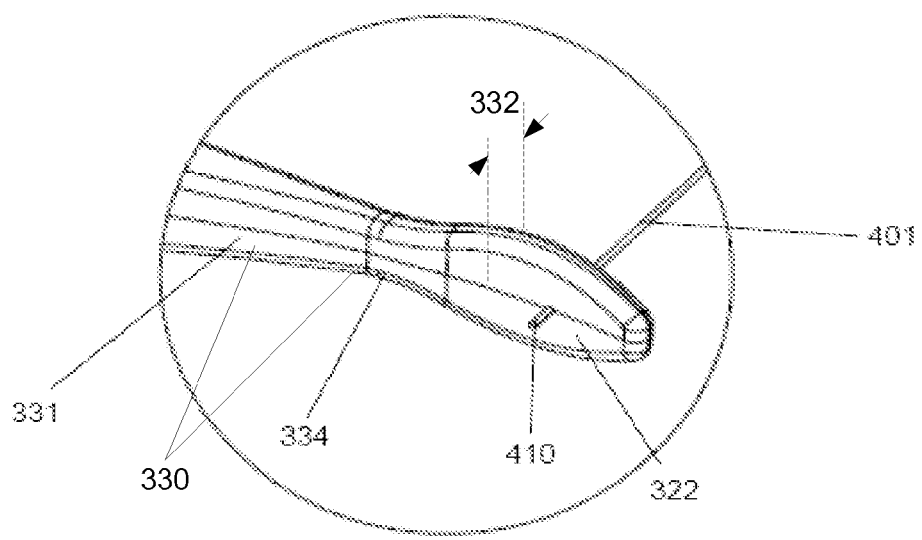
FIG. 9 is an enlarged detail view of the first floss support element of the embodiment of FIG. 7.
Figure 10:
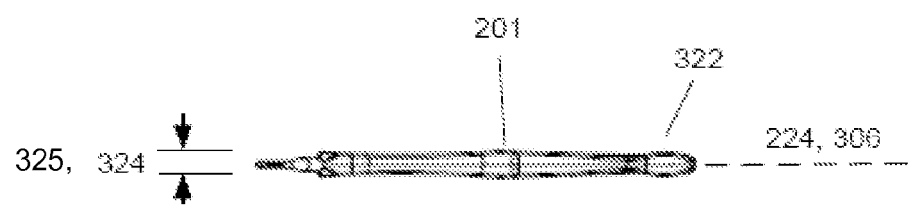
FIG. 10 is a top view of the embodiment of FIG. 7.

FIG. 9 is an enlarged detail view of the first floss support element of the embodiment of the dental flossing device 101. FIG. 10 is a top view of the embodiment of the dental flossing device. The first support section 331 has a tapered portion 334, such that, when the tapered portion is positioned in proximity to an interproximal space between the arch-wire and the teeth, the dental device may be freely pivoted with respect to the teeth without hitting the arch-wire. The first floss retention distal end 323 is wider than the tapered portion 334 of the first support section, such that there is sufficient width and strength in the first floss retention distal end to permit the attachment of a floss strand to the first floss retention distal end. In this example, the first floss retention distal end 323 is curved outwardly with respect to the second floss support element. In this example, the maximum width 325 of the first floss retention distal end is equal to the thickness of the handle.

In this example, the handle 201 comprises a flat grip portion 222 adapted to be grasped between the thumb and a finger of the user, such that the grip portion defines a grip plane 224. In this example, the grip plane is the same plane as the head plane 306. In other examples, the handle may be rotated with respect to the head, such that the head plane forms an angle with respect to the grip plane.

Figure 11A:
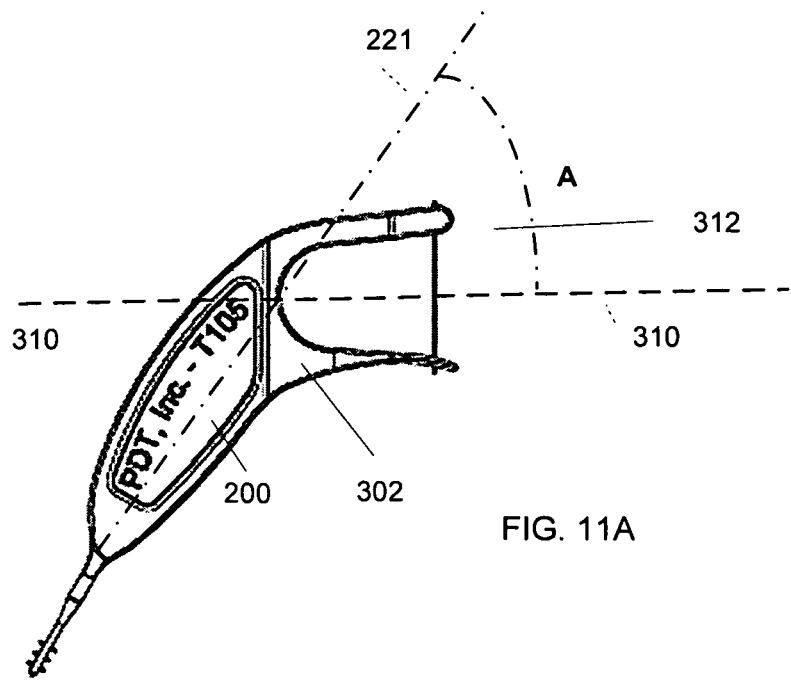
FIG. 11A is a perspective view of the embodiment of FIG. 7 showing the angle of the floss support head with respect to the handle.

FIG. 11A is a perspective view of the embodiment of FIG. 7 showing the angle of the floss support head with respect to the handle. In this example, the support head forms an angle A 312 of about 54 degrees with respect to the handle as shown by the floss support head axis of alignment 310 handle axis of alignment 221.

Figure 11B:
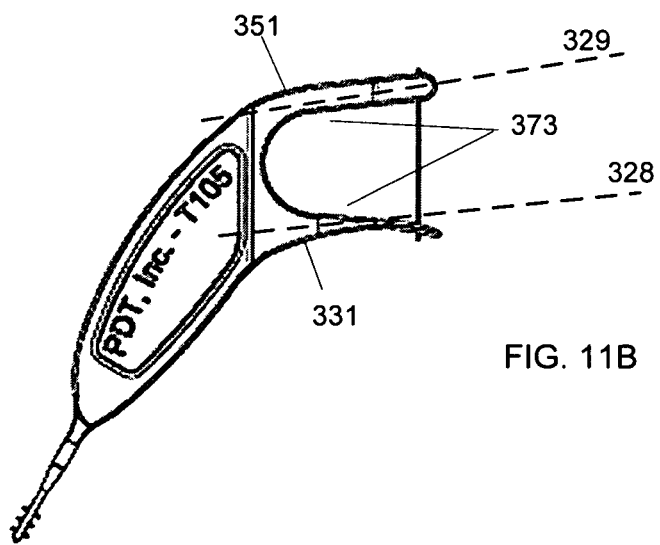
FIG. 11B is a perspective view of the embodiment of FIG. 7 showing the has a first support axis of alignment and a second support axis of alignment.

Referring to FIG. 11B, which is a front view of the dental flossing device, the first support section 331 has a first support axis of alignment 328; and the second support section 351 has a second support axis of alignment 329, such that the first floss support element and the second floss support element define a head plane 306 (not labeled) and the first support axis of alignment and the second support axis of alignment comprise the sides of the U-shape 373.

Method of Use—Bottom Teeth

Figure 12A:
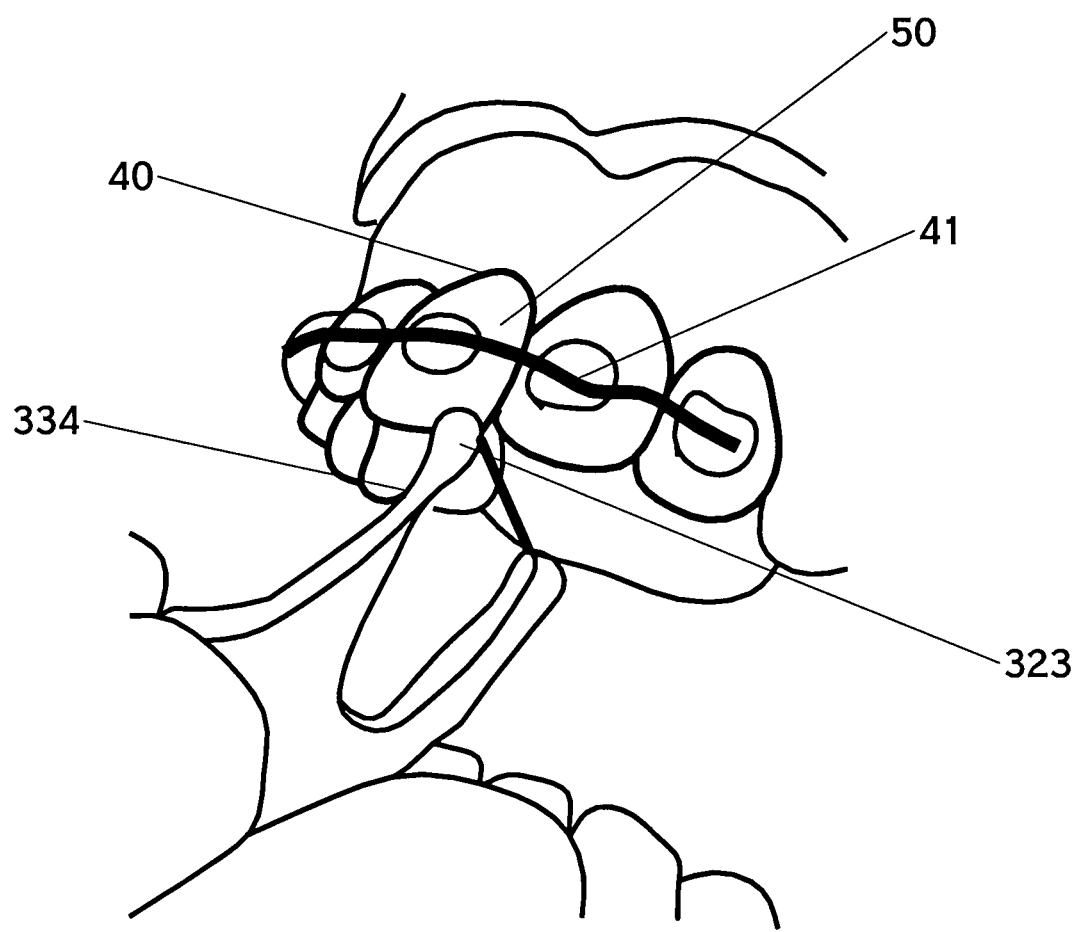
FIG. 12A is a perspective view illustrating the use of the device of FIG. 7 in a model mouth, with the device aligned for insertion behind the arch-wire.
Figure 12B:
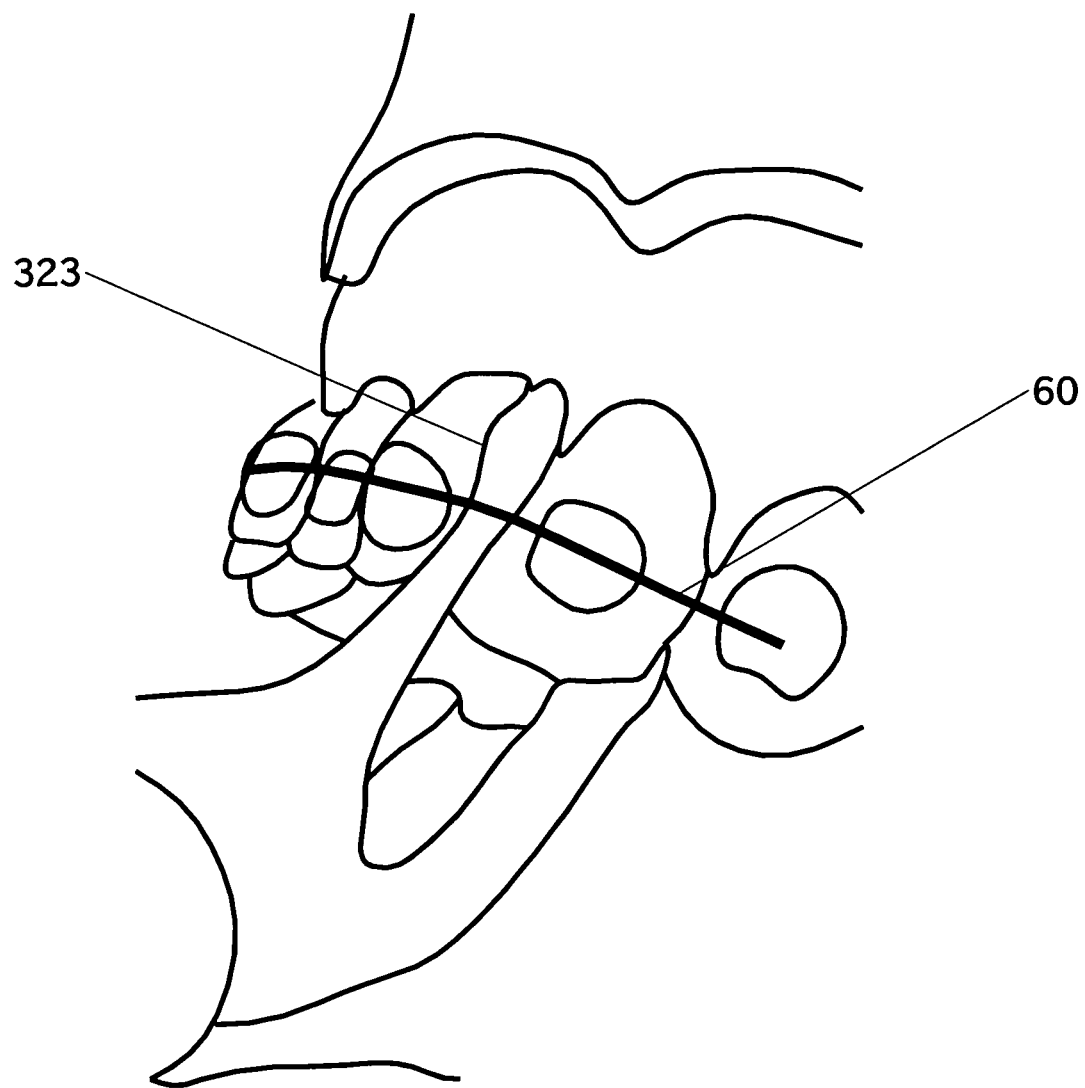
FIG. 12B is a perspective view illustrating the use of the device of FIG. 7 in a model mouth, with the device inserted behind the arch-wire.

FIG. 12A is a perspective view illustrating the use of the dental flossing device 101 in a model mouth, with the device aligned for insertion behind the arch-wire. FIG. 12B is a perspective view illustrating the use of the dental flossing device 101 in a model mouth, with the device inserted behind the arch-wire.

In this embodiment, the following steps are repeated for each interproximal space 50:

To insert the first floss support element 321 behind the arch-wire 60, the handle 201 is held so that the first floss support element is parallel to the teeth. The spatula end 323 is positioned interproximally behind the arch-wire and slid toward the gumline. If the user is flossing the tooth on the user's right of the interproximal area, then the handle is moved to the user's right. If the user is flossing the tooth on the user's left of the interproximal area, then the handle is moved to the user's left. This pivoting is permitted without interference with the arch-wire when first support section tapered portion 334 is positioned behind the arch-wire.

Assuming that the user starts with the tooth on the user's right of the interproximal area, the handle is rotated to the right. To begin the flossing operation, the handle moved down to slide the floss down into the gum sulcus or pocket. The handle is then moved up and down 2 or three times to slide the floss up and down in the gum sulcus or pocket.

To floss, the tooth on the user's left, the handle is rotated to the left. To begin the flossing operation, the handle is then moved up and down 2 or three times to slide the floss up and down in the gum sulcus or pocket.

To remove the device, the handle is rotated so the spatula end is parallel to the teeth in order to present a thin profile between the teeth and the arch-wire. The handle is then lifted to lift the first end above the arch-wire and teeth.

A pick may be attached to the opposite end of the handle and may be used to clean around orthodontic brackets.

One feature of the current invention is that the first support element 321 and the second support element 351 are longer than prior art wand type floss devices, so that the device is easier to insert in the interproximal areas.

Method of Use—Top Teeth

Each interproximal area is flossed in a manner similar to the bottom teeth, except that to insert first floss support element 321 behind the arch-wire, the handle is held slightly below the upper teeth. The first end is positioned interproximally and slid toward the gumline. The handle is rotated to the right or left as described above. To begin the flossing operation, the handle is moved up to slide the floss up into the gum sulcus or pocket. The handle is then moved up and down 2 or three times to slide the floss up and down in the gum sulcus or pocket. To remove the device, the handle is rotated so the spatula end is parallel to the teeth in order to present a thin profile between the teeth and the arch-wire. The handle is then lowered to lower the first end loop below the arch-wire and teeth.

The current invention is not limited to use by persons who wear braces. Reusable or disposable dental flossing devices having a head oriented and an angle relative to the handle permit children and adults to easily aspect all areas to be flossed without requiring fingers to be inserted in the mouth.

The current invention is not limited to the specific examples shown. Various alternatives and substitutions will be apparent to those skilled in the art without departing from the scope and fair meaning of the current invention as set forth in the description and as described by the claims.

What is claimed is:

1. A dental flossing device for providing and supporting floss to the interproximal spaces between the teeth of a user, the user having an arch-wire spaced apart from the teeth, the device comprising
 a handle, the handle having a handle axis of alignment; and
 a floss support head attached to the handle, the floss support head being formed as a U-Shape, the floss support head having a head axis of alignment oriented at an acute angle with respect to the handle axis of alignment, the floss support head comprising
 a first floss support element (331) having a first support axis of alignment, the first floss support element comprising
 a first floss retention distal end (322) having a thickness less than the distance that the arch-wire is spaced apart from the teeth, and a first support section having a thickness less than the distance that the arch-wire is spaced apart from the teeth, the first floss retention distal end comprising
 a tapered neck portion (334) between said first floss retention distal end and said first support section, said tapered neck portion having a larger cross section adjacent said first floss retention distal end and a smaller cross section adjacent said first support section, such that, when the tapered neck portion is positioned in proximity to an interproximal space between the arch-wire and the teeth, the dental device may be freely pivoted with respect to the teeth without hitting the arch-wire; and
 said first floss retention distal end being a spatula tip, such that the spatula tip is broader than the tapered neck portion and has a thickness less than the distance that the arch-wire is spaced apart from the teeth;
 a second floss support element having a second support axis of alignment, the first floss support element and the second floss support element defining a head plane, the first support axis of alignment and the second support axis of alignment comprising the sides of the U-Shape, the second floss support element comprising
 a second floss retention distal end and a second support section spaced apart from the first support element; and
 a floss strand, the floss strand having a first end affixed to the spatula tip of the first floss retention distal end, the floss strand being supported by the second floss retention distal end.

2. The dental device of claim 1 wherein the first floss retention distal end is wider than the tapered portion of the first support section, such that there is sufficient width and strength in the first floss retention distal end to permit the attachment of a floss strand to the first floss retention distal end.

3. The dental device of claim 2 wherein the first floss retention distal end is curved outwardly with respect to the second floss support element.

4. The dental device of claim 1 wherein the maximum width of the first floss retention distal end is equal to the thickness of the handle.

* * * * *